United States Patent [19]

Hosomi

[11] Patent Number: 4,973,705

[45] Date of Patent: Nov. 27, 1990

[54] METHOD FOR THE PREPARATION OF 1,3-OXATHIOLANES

[75] Inventor: Akira Hosomi, Nagasaki, Japan

[73] Assignee: Toray Silicone Company, Ltd., Tokyo, Japan

[21] Appl. No.: 242,994

[22] Filed: Sep. 9, 1988

[30] Foreign Application Priority Data

Sep. 11, 1987 [JP] Japan ................. 62-227987

[51] Int. Cl.$^5$ ................. C07D 497/10; C07D 327/04; C07D 411/10

[52] U.S. Cl. ................. 548/410; 549/30; 549/31

[58] Field of Search ............ 548/410; 549/30, 31

[56] References Cited

U.S. PATENT DOCUMENTS 4,496,600  1/1985  Parliment ................. 549/30

FOREIGN PATENT DOCUMENTS 0140884  4/1980  German Democratic Rep. ... 549/30

OTHER PUBLICATIONS

Hosomi, J.C.S. Chem. Comm., 1987, 1442.

*Primary Examiner*—Mark L. Berch
*Attorney, Agent, or Firm*—Carl A. Yorimoto; Roger E. Gobrogge

[57] ABSTRACT

A method for preparation of 1,3-oxathiolanes is described. The method comprises reacting, in a solvent, a fluoride ion source, a carbonyl compound, and a halomethyl trimethylsilylmethyl sulfide, wherein the halomethyl trimethylsilyl methyl sulfide is selected from a group consisting of chloromethyl trimethylsilylmethyl sulfide, bromomethyl trimethylsilylmethyl sulfide, or iodomethyl trimethylsilylmethyl sulfide.

13 Claims, No Drawings

METHOD FOR THE PREPARATION OF 1,3-OXATHIOLANES

BACKGROUND OF THE INVENTION

The instant invention relates to a method for the preparation of 1,3-oxathiolanes.

Methods for the preparation of 1,3-oxathiolanes by the reaction of mercapto alcohols and aldehydes or ketones under acid catalysis are in fact known. However, in these methods, one encounters the problem that high yields are unobtainable when the water by-product is not removed by an azeotropic distillation.

SUMMARY OF THE INVENTION

The instant invention was achieved as the result of extentsive research by the inventors into a high-yield method for the preparation of 1,3-oxathiolanes under mild reaction conditions.

The object of the present invention is to introduce a high-yield method for the preparation of 1,3-oxathiolanes under mild reaction conditions.

The object is achieved by means of the reaction of a fluoride ion source, carbonyl compound, and halomethyl trimethylsilylmethyl sulfide, the halomethyl group being chloromethyl, bromomethyl, or iodomethyl, in acetonitrile or tetrahydrofuran. The instant invention, because it consists of the reaction in acetonitrile or tetrahydrofuran of halomethyl trimethylsilylmethyl sulfide, in which the halomethyl group is chloromethyl, bromomethyl, or iodomethyl, plus a carbonyl compound plus a fluoride ion source, has the remarkable effect of providing a high-yield synthesis of 1,3-oxathiolanes under gentle conditions.

DESCRIPTION OF THE INVENTION

In accordance with the instant invention a method is provided for the preparation of 1,3-oxathiolanes under conditions that will be delineated herein. What is described, therefore is a method for preparation of 1,3-oxathiolanes, said method comprising reacting, in a solvent, a fluoride ion source, a carbonyl compound, and a halomethyl trimethylsilylmethyl sulfide, wherein the halomethyl trimethylsilyl methyl sulfide is selected from a group consisting of chloromethyl trimethylsilylmethyl sulfide, bromomethyl trimethylsilylmethyl sulfide, or iodomethyl trimethylsilylmethyl sulfide.

For the purposes of the instant invention, the term "halomethyl trimethylsilylmethyl sulfide" refers to a compound with the formula,

$(CH_3)_3SiCH_2SCH_2X$, wherein, X is a chlorine, bromine, or iodine. When considered from the viewpoint of reactivity, preferred halomethyl trimethylsilylmethyl sulfides are chloromethyl trimethylsilylmethyl sulfide followed by bromomethyl trimethylsilylmethyl sulfide. These halomethyl trimethylsilylmethyl sulfides can be easily synthesized by passing dry hydrogen halide for several hours with ice cooling through a mixture of trimethylsilylmethylthiol and trioxane. This is followed by the addition of hexane, dehydration, removal of the hexane, and distillation.

The carbonyl compounds can be, for example, ketones, aldehydes, ketoesters, ketoamides, and ketone acid esters. On the basis of reactivity, preferred carbonyl compounds are alpha-diketones and alpha-ketoamides, particularly the cyclic alpha-diketones and cyclic alpha-ketoamides, followed by aromatic aldehydes. Examples of the carbonyl compounds are benzaldehyde, p-chlorobenzaldehyde, p-methoxybenzaldehyde, benzil, acenaphthenequinone, isatin, N-benzylisatin, and N-methylisatin.

The carbonyl compound is preferably dried prior to its introduction into the reaction.

Examples of fluoride ion sources are cesium fluoride, rubidium fluoride, lithium fluoride, $(n-C_4H_9)_4NF$, and KF-18-crown-6. Cesium fluoride is most preferred from the standpoint of reactivity. Furthermore, the fluoride ion source is also preferably dried prior to its introduction into the reaction.

Acetonitrile and tetrahydrofuran are solvents which serve to dissolve, in whole or in part, the starting halomethyl trimethylsilylmethyl sulfide, carbonyl compound, and fluoride ion source. Acetonitrile is preferred from a consideration of reaction yield. These solvents are preferably dried prior to their introduction to the reaction.

To synthesize 1,3-oxathiolanes by the reaction of halomethyl trimethylsilylmethyl sulfide, carbonyl compound, and fluoride ion source in acetonitrile or tetrahydrofuran, these starting materials and solvent are placed in a reactor and stirred with the exclusion of moisture. The reaction temperature is preferably room temperature, but the reaction may optionally be heated to the boiling point of acetonitrile or tetrahydrofuran as the case may be.

The reaction time will vary with the reaction temperature and the nature of the starting compounds. It will typically exceed 10 hours for reactions at room temperature. While it will generally require 15 to 100 hours, as long as 200 hours or more may be required.

With regard to the ratios at which the starting reactants are taken, the molar ratio between the halomethyl trimethylsilylmethyl sulfide and carbonyl compound is preferably in a range from about 1.0:1.0 to 4.0:1.0. The molar ratio between the fluoride ion source and carbonyl compound is preferably in a range from about 1.0:1.0 to 3.0:1.0.

The 1,3-oxathiolane is then isolated from the reaction solution after completion of the reaction. Because 1,3-oxathiolanes are soluble in acetonitrile or tetrahydrofuran along with unreacted starting materials and by-products, ether plus water or preferably aqueous sodium bicarbonate is first added, this is shaken, and the ether layer is separated after standing. After this step has been repeated two to three times, the ether layer is dried over a dehydrating agent and the ether is then removed. The residue is then fractionated by thin-layer chromatography.

The mechanism for the synthesis of 1,3-oxathiolanes by the action of halomethyl trimethylsilylmethyl sulfide on a carbonyl compound in the presence of a fluoride ion source in acetonitrile or tetrahydrofuran is theorized by the inventor to consist of a [3+2] cycloaddition at the carbonyl group of the carbonyl compound by the thiocarbonyl ylide synthon generated from the halomethyl trimethylsilylmethyl sulfide by the action of the fluoride ion. However, the instant invention is not limited by this theory.

So that those skilled in the art may better understand and appreciate the instant invention, the following examples are presented. These examples are presented as being illustrative and are not to be construed as limiting the instant invention as claimed herein.

The instant invention will be explained on the basis of reference and illustrative examples. In the reference and illustrative examples, the infrared absorption spectrum (IR) was taken using the KBr tablet method, the ultraviolet absorption spectrum (UV) was measured in 95% ethanol, and the nuclear magnetic resonance spectrum ($^1$HNMR) was measured using tetramethylsilane as internal reference. The mass spectrum (MS) was taken using low-resolution and high-resolution mass analysis, and TLC denotes thin-layer chromatography.

EXAMPLE 1

Synthesis of chloromethyl trimethylsilylmethyl sulfide 12.0 g (0.10 mol) trimethylsilylmethylthiol and 3.2 g (0.035 mol) trioxane were placed in and mixed in a round-bottom flask. Dry hydrogen chloride was passed through the mixture for 4 hours with ice cooling. 50 ml hexane was then added, and the hexane was removed after drying over sodium sulfate.

Distillation afforded 11.7 g (0.069 mol) of the target chloromethyl trimethylsilylmethyl sulfide. The recovered product had a boiling point of 75° C. at 20 mmHg.

Analytical results were as follow:

$^1$HNMR (CCl$_4$): delta 0.01 (s, 9H), 2.00 (s, 2H), 4.80 (s, 2H)

Elemental analysis was as follow: C 35.81 (calculated value 35.59) H 7.43 (calculated value 7.76)

Mass spectral analysis gave the following results: (m/z) 70 eV: 170 (6), 168 (M+, 14), 153 (7), 133 (6), 120 (5), 11.9 (37), 95 (13), 93 (33), 79 (10), 75 (8), 74 (9), 73 (100), 61 (5), 60 (70), 59 (16), 46 (7), 45 (20), 44 (23), 43 (15)

EXAMPLE 2

237 mg (1 mmol) N-benzylisatin and 304 mg (2 mmol) cesium fluoride were placed in a 50 ml two-neck round-bottom flask and dried in vacuo using a vacuum pump. Pressure in the flask was then released using dry argon gas. A 10 ml acetonitrile solution of 338 mg (2 mmol) chloromethyl trimethylsilylmethyl sulfide was then added to the flask and then stirred for 22 hours at room temperature using a magnetic stirrer.

After completion of the reaction, 20 ml diethyl ether was added, followed by the addition of saturated aqueous sodium bicarbonate for hydrolysis.

The separated aqueous layer was then extracted with diethyl ether (three extractions with 10 ml ether per extraction). The combined ether layer was dried over anhydrous sodium sulfate, and the solvent was then removed using an evaporator. The residue was subjected to silica gel thin-layer chromatography (benzene, Rf=0.45) to obtain 257 mg (0.86 mmol, yield=86%) of the target 1,3-oxathiolane reported in Table 1 as Experiment 7.

The analytic data is reported below.

$^1$HNMR (CDCl$_3$): delta 3.0–3.8 (2H, m), 4.9 (2H, s), 5.1–5.7 (2H, m), 6.5–7.8 (9H, m)

Elemental analysis: C 68.70 (calculated 68.66) H 5.07 (calculated 5.08) N 4.67 (calculated 4.71) S 10.93 (calculated 10.78)

EXAMPLE 3

Reactions were tun under the same conditions as in Example 1, using 7 different carbonyl compounds to obtain the 1,3-oxathiolanes reported in Table 1. Table 1 is a summary of the seven runs made, designating the runs as Experiments 1, 2, 3, 4, 5, 6, and 8, respectively.

For each run is listed the carbonyl compound, the reaction or stirring time in hours, and the structure and yield of the desired product.

The analytical values for each 1,3-oxathiolane and the thin-layer chromatographic conditions are reported below.

Experiment Number 1
TLC (PhH/HeX=¼) Rf 0.46
$^1$HNMR (CCl$_4$): 2.8–3.4 (2H, m), 4.8–5.3 (3H, m), 7.2–7.5 (5H, m)
MS: 166 (M+), 135, 104, 91, 77

Experiment Number 2
TLC (PhH/H=¼) Rf 0.54
$^1$HNMR (CCl$_4$): 2.7–3.3 (2H, m), 4.8–5.1 (3H, m), 7.3 (4H, s)
MS: 200 (M+), 170, 135, 125

Experiment Number 3
$^1$HNMR (CCl$_4$): 2.98–3.44 (2H, m), 3.80 (3H, s), 4.76–5.14 (3H, m), 7.25–7.38 (4H, m)

Experiment Number 4
$^1$HNMR (CDCl$_3$): delta 2.88 (1H, dd, J=11, 13 Hz), 3.30 (1H, dd, J=7.13 Hz), 3.3–4.0 (1H, m), 4.7–5.1 (2H, m), 5.95 (2H, s), 6.8–6.9 (4H, m)

Experiment Number 5
TLC (H/E=5/1) Rf 0.56
$^1$HNMR (CCl$_4$); 2.75 (1H, d, J=14 Hz), 4.18 (1H, d, J=14 Hz), 4.62 (1H, d, J=8 Hz), 4.98 (1H, d, J=8 Hz), 7.0–8.2 (10H, m)
MS: 270 (M+)

Experiment Number 6
TLC (PhH) Rf 0.5
$^1$HNMR (CDCl$_3$): 2.9–3.8 (2H, m), 5.0–5.6 (2H, m), 7.5–8.4 (6H, m)
MS: 242 (M+)
Elemental analysis: C 69.30 (calculated 69.40) H 4.21 (calculated 4.16) S 13.48 (calculated 13.23)

Experiment Number 8
TLC (H/E=1/1) Rf 0.36
$^1$HNMR: 2.7−3.7 (5H, m), 4.9−5.4 (2H, m), 6.5−7.5 (4H, m)
Elemental analysis:
C 59.77 (calculated 59.71)
H 5.00 (calculated 5.01)
N 6.21 (calculated 6.33)
S 14.73 (calculated 14.49)

TABLE 1

| Exp. no. | carbonyl compound | stirring time (hours) | product structural formula | yield |
|---|---|---|---|---|
| 1 | C$_6$H$_5$CHO | 94 | 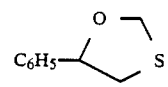 | 35 |

TABLE 1-continued

| Exp. no. | carbonyl compound | stirring time (hours) | product structural formula | yield |
|---|---|---|---|---|
| 2 | p-ClC₆H₄CHO | 194 | p-ClC₆H₄─⟨O—CH₂—CH₂—S⟩ | 54 |
| 3 | p-MeOC₆H₄CHO | 71 | p-MeOC₆H₄─⟨O—CH₂—CH₂—S⟩ | 83 |
| 4 | piperonal (methylenedioxybenzaldehyde) | 192 | corresponding 1,3-oxathiolane | 49 |
| 5 | C₆H₅COCOC₆H₅ | 38 | C₆H₅CO, C₆H₅ substituted 1,3-oxathiolane | 61 |
| 6 | acenaphthenequinone | 19 | corresponding spiro 1,3-oxathiolane | 76 |
| 7 | N-benzylisatin | 22 | corresponding spiro 1,3-oxathiolane (N-CH₂C₆H₅) | 86 |
| 8 | N-methylisatin | 44 | corresponding spiro 1,3-oxathiolane (N-CH₃) | 66 |

What is claimed is:

1. A method for preparation of 1,3-oxathiolanes, said method comprising reacting, in a solvent, a fluoride ion source, a carbonyl compound, and a halomethyl trimethylsilylmethyl sulfide, wherein the halomethyl trimethylsilyl methyl sulfide is selected from a group consisting of chloromethyl trimethylsilylmethyl sulfide, bromomethyl trimethylsilylmethyl sulfide, or iodomethyl trimethylsilylmethyl sulfide.

2. A method for preparation of 1,3-oxathiolanes as described in claim 1, wherein the halomethyl trimethylsilylmethyl sulfide is selected from a group consisting of chloromethyl trimethylsilylmethyl sulfide or bromomethyl trimethylsilylmethyl sulfide.

3. A method for preparation of 1,3-oxathiolanes as described in claim 1, wherein the halomethyl trimethylsilylmethyl sulfide is chloromethyl trimethylsilylmethyl sulfide.

4. A method for preparation of 1,3-oxathiolanes as described in claim 1, wherein the fluoride ion source is cesium fluoride.

5. A method for the preparation of 1,3-oxathiolanes as described in claim 1, wherein the carbonyl compound is selected from the group consisting of ketones and aldehydes.

6. A method for preparation of 1,3-oxathiolanes as described in claim 5, wherein the carbonyl compound is selected from a group consisting of alpha-diketones, alpha-ketoamides, and aromatic aldehydes.

7. A method for preparation of 1,3-oxathiolanes as described in claim 6, wherein the alpha-diketones are cyclic alpha-diketones.

8. A method for preparation of 1,3-oxathiolanes as described in claim 6, wherein the alpha-ketoamides are cyclic alpha-ketoamides.

9. A method for the preparation of 1.3-oxathiolanes as described in claim 5 wherein the ketone is selected from the group consisting of ketoesters and ketoamides.

10. A method for preparation of 1,3-oxathiolanes as described in claim 1, wherein the molar ratio of the halomethyl trimethylsilylmethyl sulfide relative to the carbonyl compound is in a range from about 1.0:1 to 4.0:1.

11. A method for preparation of 1,3-oxathiolanes as described in claim 1, wherein the molar ratio of the fluoride ion source relative to the carbonyl compound is in a range from about 1.0:1 to 3.0:1.

12. A method for preparation of 1,3-oxathiolanes as described in claim 1, wherein the fluoride ion source, the carbonyl compound, and the halomethyl trimethylsilylmethyl sulfide are heated at room temperature or greater.

13. A method for preparation of 1,3-oxathiolanes as described in claim 1, wherein the fluoride ion source, the carbonyl compound, and the halomethyl trimethylsilylmethyl sulfide are contacted for greater than about 10 hours.

* * * * *